US008155925B2

(12) United States Patent
Bodlaender et al.

(10) Patent No.: US 8,155,925 B2
(45) Date of Patent: Apr. 10, 2012

(54) DISPOSABLE ASSAY DEVICE WITH REMOVABLES MODULES AND REMOTE DATA TRANSFER SYSTEM

(75) Inventors: Maarten Peter Bodlaender, Eindhoven (NL); Wilhelmus Johannes Joseph Stut, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 531 days.

(21) Appl. No.: 12/305,389

(22) PCT Filed: Jun. 20, 2007

(86) PCT No.: PCT/IB2007/052383

§ 371 (c)(1),
(2), (4) Date: Dec. 18, 2008

(87) PCT Pub. No.: WO2008/001279

PCT Pub. Date: Jan. 3, 2008

(65) Prior Publication Data

US 2009/0132204 A1 May 21, 2009

(30) Foreign Application Priority Data

Jun. 28, 2006 (EP) .................................... 06116179

(51) Int. Cl.
*G06F 15/00* (2006.01)
*C12M 1/34* (2006.01)
*G01D 11/24* (2006.01)
*B01J 19/00* (2006.01)

(52) U.S. Cl. .......... 702/188; 435/287.1; 73/431; 422/50

(58) Field of Classification Search .................. 702/188; 422/50, 401; 73/431; 435/287.1
See application file for complete search history.

(56) References Cited

U.S. PATENT DOCUMENTS

| | | | | |
|---|---|---|---|---|
| 5,395,594 | A | 3/1995 | Nokihara | |
| 2002/0124896 | A1 | 9/2002 | O'Connor | |
| 2003/0012697 | A1 | 1/2003 | Hahn | |
| 2005/0140091 | A1 | 6/2005 | Brickwood | |
| 2005/0145048 | A1 | 7/2005 | Moir | |
| 2005/0221504 | A1 | 10/2005 | Petruno | |
| 2009/0104074 | A1 * | 4/2009 | Bodlaender et al. | 422/50 |

FOREIGN PATENT DOCUMENTS

| | | | |
|---|---|---|---|
| CA | 2516490 | A1 | 5/2004 |
| EP | 0972196 | B1 | 1/2000 |
| WO | 9533996 | A1 | 12/1995 |
| WO | 0240708 | A2 | 5/2002 |
| WO | 2004052540 | A2 | 6/2004 |

* cited by examiner

*Primary Examiner* — Bryan Bui

(57) ABSTRACT

Disposable assay device, comprising a carrier having a first carrier part (3) with a respective sample-receiving area (w) for receiving a sample to be tested, and having at least a second carrier part (9), the assay device being configured for transmitting assay data or information to a remote receiving system (20), and the device comprising at least two first carrier parts, said first carrier parts (3, 5) being independently removable from the second carrier part (9).

16 Claims, 3 Drawing Sheets

DISPOSABLE ASSAY DEVICE WITH REMOVABLES MODULES AND REMOTE DATA TRANSFER SYSTEM

FIELD OF THE INVENTION

The invention relates to a disposable assay device, comprising a carrier having a first carrier part with a respective sample-receiving area for receiving a sample to be tested, and having at least a second carrier part, the assay device being configured for transmitting assay data or information to a remote receiving system.

BACKGROUND OF THE INVENTION

International patent application WO 95/33996 of Zwanziger et al. discloses a home test kit for use in testing for a disease or a physiological condition, with telephone verification of test results. The known home test kit facilitates the delivery of any necessary counseling as a result of the outcome of a test. During use, an individual can obtain a sample of physiological fluid from him or herself. The sample can be introduced into an assay device to produce a coded pattern indicative of the presence or absence of the disease. The individual can transmit the coded pattern to a remote location for interpretation, for example by telephone. Then, the individual can receive, from the remote location, an interpretation of the coded pattern together with any counseling which may be appropriate in view of the interpretation of the coded pattern. In this way, the remote location has to be used for interpretation of the test.

Also, from EP972196B1 a different assessment device is known, where a recording part is detachable from an assay part. This known device is provided with a test-ready indicator. Here, the results of the assay are also not directly available to the user.

The present invention aims to provide an improved assay device and assay method.

SUMMARY OF THE INVENTION

According to an embodiment of the invention, the device is characterized in that the device comprises at least two first carrier parts, wherein the first carrier parts are independently removable from the second carrier part.

By providing at least two independently removable first carrier parts, cross-contamination can be avoided, and at least two samples (or portions of the same sample) can be tested, using the same device. Thus, only one device can be provided to a user to perform at least two tests, in a reliable manner. Besides, contamination of the second carrier part by a sample can be avoided in this way, so that the second carrier part can be sent by mail and/or handled safely by personnel of a processing facility. Moreover, the device can be made relatively cheap, for example by providing the device without a test result display device, or without a test result display-processing facility.

Besides, an embodiment of the invention provides an assay method, utilizing at least one device according to the invention, the method comprising:

applying one or more samples to the first carrier parts of the device to test the samples for the presence of one or more analytes;

storing resulting test results in a memory of the device, without disclosing the results; and removing each first carrier part from a remaining device part after having used that first carrier part.

This method can provide above-mentioned advantages.

BRIEF DESCRIPTION OF THE DRAWINGS

Further advantageous embodiments of the invention are described in the dependent claims. These and other aspects of the invention will be apparent from and elucidated with reference to the embodiments described hereafter.

DETAILED DESCRIPTION

In the present application, similar or corresponding features are indicated by similar or corresponding reference signs.

There are 20.8 million people in the United States, or 7% of the population, who have diabetes. While an estimated 14.6 million have been diagnosed with diabetes, 6.2 million people (or nearly one-third) are unaware that they have the disease.

Today, in order to determine whether or not a person has pre-diabetes or diabetes, health care providers conduct a Fasting Plasma Glucose Test (FPG) or an Oral Glucose Tolerance Test (OGTT). Either test can be used to diagnose pre-diabetes or diabetes.

Instead of the person having to go to the care provider, the person can perform the test at home. For example, the person may put a blood sample on a device that is capable of conducting a glucose test.

For a number of medical measurement protocols, it is necessary to perform a sequence of measurements instead of only one measurement. While it is known in the art to include multiple application wells on an assay part of an assay device, the existing technology is not suitable for measurement protocols that require significant amounts of time to pass between each measurement. For example, to have a better quality assessment, it can be beneficial to repeat the measurement for 3 consecutive days. In a known device (see EP972196B1), the assay part can only be detached at the end of this period. During this period there is the risk of bio-contamination as the first application well contains biomaterial after the first assessment. This risk can be avoided by independently removable application wells w, as can be seen from the present embodiments.

Figure 1:
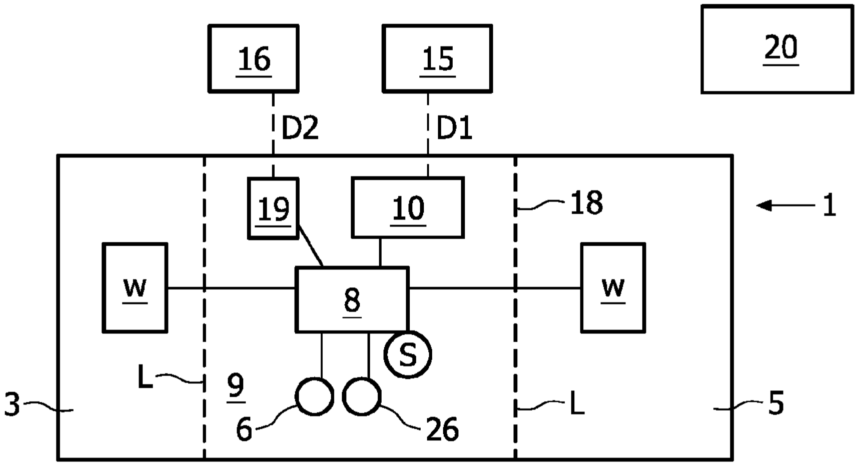
FIG. 1 schematically shows an assay device according to a first embodiment of the invention.

FIG. 1 schematically shows an embodiment of a disposable assay device 1. The device 1 comprises a carrier or substrate, having two first carrier parts 3, 5, with respective sample-receiving areas w for receiving samples to be tested, and having a second carrier part 9 comprising a memory device 10 configured to store assay results relating to tested samples. The carrier 3, 5, 9 can be made of various materials, for example a suitable paper or paper-like material, plastic and/or other materials. Also, the first carrier parts 3, 5 are independently removable (i.e. independently with respect to each other) from the second carrier part 9 to independently remove the respective application wells w from the second carrier part 9. Advantageously, the assay device 1 is configured for transmitting assay data or information to a remote receiving system 20 (see FIG. 1). For example, the device 1 can be configured to store the assay results without displaying the results to a user of the device 1 (here, a user of the device 1 is generally a person who, during use of the device 1 to assay one or more samples, applies a mentioned sample to an application well w of the device 1). The assay device 1 can be configured to assay one or more samples, and to provide at least one assay result based on the assaying of the one or more samples.

Since the device 1 is configured for transmitting assay data or information to a remote receiving system 20, assay results are preferably not made known directly to the user of the device. Therefore, the user can be kept motivated to return the second carrier part 9, which may be provided with a memory device and/or a controller and/or other components, to, for example, a remote central processing facility 20.

For example, the device 1 can be used to assay individual users of an assay system, for screening purposes. Individuals to be tested by the device 1 can be human individuals. However, alternatively, the devices can be configured to assay animals or vegetation.

Besides, assays to be conducted with the device 1 can involve screening of certain other areas or locations, for example screening of environments (air, water, soil, etc.) for contamination, certain substances and/or organisms.

The assay device 1 can be configured to detect various types of analytes. For example, analytes to be determined can include glucose, pregnancy-related analytes, cholesterol, drugs, biotoxins, diseases, cardiac markers, chemicals, hormones, proteins, and/or other analytes. Other analytes can include certain substances, toxic matter, environmental contamination and/or different analytes.

The assay device 1 can be configured to assay various types of samples, for example samples of blood, bodily fluid, saliva, urine, plasma, serum and/or other sample types, as will be clear to the skilled person. Also, the different application wells w can be used to receive different samples, for example in a predetermined sequence and/or after predetermined time periods. Alternatively, different application wells w of the device can be used to receive parts of the same sample, if desired.

Besides, advantageously, the assay device 1 is portable, lightweight, and compact, for example having a relatively flat credit card format, or sheet-like configuration. For example, the assay device 1 can be configured to be sent to users in a simple envelope or package, or by or as part of a letter, by regular mail.

The assay devices 1 can each be configured in various ways to conduct an assay on a sample, as will be clear to the skilled person. For example, the assay device 1 can be provided with one or more suitable enzymes, antibodies, binders or binding agents, a labeling substance, and/or microorganisms, which can be responsive to a specific analyte to be searched for. An analyte and/or analyte-dependent modifications can be detected, for example, optically, electrochemically, by electrical resistance measurement, and/or in a different way, by the assay device 1. Testing of the analyte can be conducted, for example, at the respective sample-receiving areas (or sample wells) w, or at other locations of the assay device.

In the present embodiment, the first and/or second carrier parts comprise microelectronics configured to assay the samples, provide respective test results and store the results in the memory 10. To this aim, for example, the microelectronics can cooperate with and/or be electrically connected to the mentioned sample receiving wells w in a suitable manner, to carry out the assaying of the samples, as will be clear to the skilled person. Preferably, the second carrier part 9 is provided with a major part (for example more than 50% and particularly at least 90%) of the microelectronics, for example with substantially all of the microelectronics.

The testing can be controlled, for example, by a suitable controller 8 of the device. In a more detailed analysis of the architecture of the device, it can comprise a controller 8, connected to an A/D convertor through a digital connect, that is connected to application wells w through one or more analog connects 18. Preferably, the A/D convertor is provided on the second carrier part 9, for example via integration with the controller 8, for cost saving and to enable re-using the A/D convertor over multiple application wells, and recycling it.

A mentioned test result, which is stored in the memory device 10, can include various types of results, for example a numerical value or true-false value (or "positive-negative", 0-1, True-False) relating to a successfully conducted sample assaying. On the other hand, in case an assay is inconclusive or fails, such as due to a certain device failure, a test result can be "assay inconclusive", "assay failed", "device failure" or a similar result.

In a further embodiment (see FIGS. 4 and 5), the carrier can be provided with a low-cost write-once display, configured to subsequently provide operating steps to be taken by a user of the device 1, during use. Besides, in an embodiment, the second carrier part can be provided with a user interface, preferably, comprising multiple-choice buttons (also depicted in FIGS. 4 and 5).

Further, the carrier can advantageously be provided with a user guide configured to guide a user in the application of samples to the first carrier parts, the user guide preferably being arranged to indicate a predetermined sequence of use of the first carrier parts. For example, the user guide can be provided in printing or via audiovisual means, such as a display and/or loudspeaker that is/are controllable by the controller 8, to display and/or voice user guidance instructions.

Each sample-receiving area w can be provided to receive a respective sample. Detection areas can be provided for testing the samples that have been received at the receiving area 3, during use. The first carrier parts 3, 5 and/or second carrier part 9 can be provided with such detection areas. For example, an assay device 1 can comprise a plurality of sample-receiving areas w and one respective detection area, the detection area for example being located on the second carrier part 9. Alternatively, on/in the assay device 1, one sample-receiving area w can be associated with several respective detection areas, for example to assay one sample, received on that receiving area w, for different analytes. Besides, an assay device 1 can comprise several sample-receiving areas and several respective detection areas, to test several samples. For example, sample-receiving areas w and detection areas can be integrated with each other, or be spaced apart from each other. In the latter case, for example, sample conductors can be provided, for example capillary channels, to conduct one or more samples, or parts thereof, from one or more receiving areas w to one or more detection areas, for example by capillary action, gravity, or in a different manner. Besides, for example, the assay device can be manipulated, for example via folding or bending, to bring a sample-receiving area into contact with a detection area. Each assay device 1 can also be configured in a different manner.

In an embodiment, as an example, the two first carrier parts 3, 5 can be configured to carry out the same assay test, particularly to test a sample for the same analyte. Alternatively, the first carrier parts 3, 5 can be configured to carry out different assay tests, particularly to test samples for different analytes.

Also, each of the assay devices 1 can be configured to provide at least one assay result based on the assaying of the one or more samples. The mentioned controller 8 of the device 1, for example a microelectronic processor or CPU (Central Processing Unit) 8, can be configured to control and process the assaying of samples, which are received at the receiving areas w. In this case, the memory 10 is controllable by the controller or processor 8 to store the test results. As an example, the controller 8 and memory 10 can be integrated with each other, or can be separate components. Also, for example, the embodiment of FIG. 1 can comprise a so-called lab-on-a-chip system, and, for example, the controller 8 can comprise a lab-on-chip processor which can at least partly include a mentioned detection area.

Besides, the assay device can be provided with a test result transmitter 19 configured to transmit a test result to an external test result receiver 16. Here, for example, data transmission between the transmitter 19 and receiver 16 (which data transmission is schematically indicated by a dashed line D2) can take place via suitable wiring and/or wirelessly, for example using electric, electromagnetic and/or optical signals, a network interface or digital output, or differently.

Advantageously, the memory 10 can be read by an external memory-reading device 15 for obtaining the test result from the assay device 1. For example, data transmission between the memory 10 and reading device 15 (schematically indicated by a dashed line D1) can take place via suitable wiring and/or wirelessly, for example using electric, electromagnetic and/or optical signals, via a mentioned test result transmitter 19, or differently.

A mentioned external test result receiver 16 and memory reader 15 can be configured in various ways, and can include a dedicated docking station for docking the assay device 1C, a computer, a personal digital assistant (PDA), a mobile phone, and/or can be part of a remote receiving system 20, and/or can be configured differently. For example, in an embodiment, the external test result receiver 16 and memory reader 15 can be integrated with each other.

Components of the assay device 1 can be powered in various ways, for example by a solar cell, a battery, by charging, by inductance, by self-powering or capillary action, by a storage capacitor, by power storage via motion and/or a winding mechanism, or differently.

In the present embodiment, a test result storage carrier part 9 of the device 1, for example comprising the mentioned memory 10, and preferably comprising the processor 8 and transmitter 19, might be separable from each respective sample-receiving area w. Also, as an option, an assay device 1 can be provided with a test ready indicator 6, for example a LED (light emitting diode) or speaker or otherwise, to indicate when an assay of a sample is completed. In the present embodiment (see FIG. 1), the second carrier part 9 comprises the test ready indicator 6.

In an embodiment of the invention, the assay device 1 provides assay data or information, the assay data or information relating to, being based on and/or comprising one or more assay results of the assays carried out by the device 1. Advantageously, the device 1 is configured to keep the test result secret to the user of the device, similar to devices known from WO 95/33996. For example, the device 1 can be configured to provide the user with a code that is to be sent to a central receiving system 20.

The skilled person will appreciate that the receiving system 20 can be configured in various ways. As an example, the receiving system 20 can be configured to receive assay data or information (which can comprise the afore-mentioned code), the assay data or information relating to, being based on and/or comprising one or more assay results of the assay devices 1 and/or comprising information that the assaying has failed. Transmission of the mentioned assay data or information (or code) to the central receiving system 20 can take place, for example, by means of electronic transmission, transmission via a computer and/or telephone network, transmission via a communication connection between a user communication terminal and a communication terminal of the receiving system 20, transmission via regular mail and or transmission via locally available test result collection facilities, depending for example on the configuration of the respective assay device 1. Also, for example, the user can send the whole assay device 1, or preferably only the memory comprising part 9 thereof, containing assay data or information, to a remote receiving system 20.

For example, the receiving system 20 can be provided with a computerized call-receiving system, and/or voice response system, configured to receive calls from the users, for example to receive the assay data from the users, communicate with users and/or return test result-related information back to the users. Besides, in an embodiment, the receiving system 20 can be configured to cooperate with or be provided with an assay device distribution system to distribute one or more assay devices 1 to a user, for example depending on received assay data or information of an assay device 1 used earlier by that user.

Also, for example, the receiving system 20 can at least be configured to determine, using received assay data or information, whether a respective assay result of an assay device 1 is a negative or positive assay result, and/or whether the result is inconclusive, and/or whether the assaying has failed and optionally a/the reason(s) why the assaying has failed. Then, in a further elaboration, a distribution system/receiving system 20 can be configured to distribute at least one further assay device to a user U of a prior assay device, in case the receiving system 20 has determined that a respective assay result of the prior assay device 1 is a positive assay result, and/or an inconclusive result. For example, a more accurate assay device can be sent to the user, who provided a positive or inconclusive test result using a prior assay device, to confirm the positive test result, or to redo the assay, respectively, with higher accuracy.

Besides, in an embodiment, the receiving system 20 can at least be configured to determine, using received assay data or information, at least one type of deviation concerning received assay data or information with respect to threshold data or information, estimated data or information, and/or expected data or information. Also, in an embodiment, the receiving system 20 can be configured to receive at least removed parts 3, 5 of used assay devices 1, and to perform at least one of the following: detect damage and/or malfunction of received assay devices or of parts thereof, read data or information from received assay devices or parts thereof, recycle received assay devices 1 or parts thereof. For example, to detect damage and/or malfunction of received assay devices or of parts thereof, the receiving system can be provided with suitable sensors and/or detectors, as will be clear to the skilled person. The receiving system 20 can be configured, for example, to detect a color and/or optically detectable test result indicators of a received assay device or part thereof.

In the embodiment of FIG. 1, the device 1 is provided with a central second part 9 having first parts 3, 5 extending on opposite sides of the second part 9. Both first carrier parts 3, 5 are detachably coupled to the second carrier part 9. Such a detachable coupling can be configured in various ways. For example, the carrier can be provided with weakening lines or perforation lines L, extending between the first and second carrier parts 3, 5, 9 for independently removing the first carrier parts from the second carrier part. The weakening lines or perforation lines L are such that a user can tear off or break off each first carrier part 3, 5 from the second memory comprising part 9 via those lines.

Preferably, the assay device 1 is configured to detect the removal of a first carrier part 3, 5 from the second part 9. Also, preferably, the device 1 is configured to record a time of the removal of the first assay part in the memory device 10. Such detection and/or time recording can be carried out, for example, by the controller 8. Detection of removal of a first carrier part 3, 5 can be achieved using, for example, respective electrically conducting detection lines or loops (see FIG. 5) that are coupled to the controller 8 and that are interrupted or broken when a respective first carrier part 3, 5 is removed from the second part 9.

In a further embodiment, the device 1 can be configured to record each assay result in combination with identification information of a respective first carrier part 3, 5, leading to that assay result (i.e., the first carrier part 3, 5 which received a respective sample), in the memory device 10. Also, the device 1 can be configured to record each assay result in combination with time information concerning a respective assay, leading to that assay result, in the memory device 10. Other types of information can also be stored in the memory device 10, for example assay context information. For example, the assay device 1 can be configured to monitor assay context before, during and/or after assaying a mentioned sample, and preferably to store the results of such monitoring in the memory device 10. For example, the assay device 1 can be provided with one or more assay context sensors to detect temperature, humidity, contamination and/or other assay context factors. As an example, one or more such sensors can be integrated in the controller 8, or can be connected thereto in a suitable manner.

During use of the embodiment of FIG. 1, the device 1 can be provided to a user, for example by postal delivery, by handing out or in a different manner. The user can use the device 1 (for example at home or in another suitable location), in an assay method, by applying one or more samples to the application wells w of the first carrier parts 3, 5 of the device 1 to test the samples for the presence of one or more analytes. Test results, relating to the testing of the samples, are stored in the memory 10 of the device, without displaying or otherwise disclosing the results to the user. Preferably, the user removes each first carrier part 3, 5 from a remaining device part after having used that first carrier part. Thus, cross-contamination can be avoided, and all assay results can be stored in the same memory 10. After both first carrier parts 3, 5 have been used and removed, the remaining second part 9 can be returned to a central receiving/processing facility to deliver the memory 10 and its results. Alternatively, such results can be sent using suitable communication means, as mentioned above. Thus, a sequence of measurements can be performed instead of only one measurement, in a safe, efficient and accurate manner. For example, a better quality assessment can be obtained when the measurement is repeated after a predetermined time period of for instance 1 day (circa 24 h).

For example, the first carrier parts 3, 5 of the device can be used in sequence, with a predetermined intermediate time period. The device 1 can be configured to indicate this time period, for example via a suitable display. Also, the device 1 can be provided with a timer for timing the lapsing of the predetermined time period. The device can be configured to indicate to the user when the predetermined time period has lapsed to encourage the user to use the next first carrier part for a subsequent assay.

The embodiment of FIG. 1 provides the advantage that the user can use any application wells w first, as they can be independently detached. If the different assay parts contain different tests, this allows freedom in the order in which tests are taken. Besides, all first carrier parts can be the same in set-up, and wiring of electronic parts can be relatively straightforward. This simplifies the card design and lowers material costs.

Figure 2:
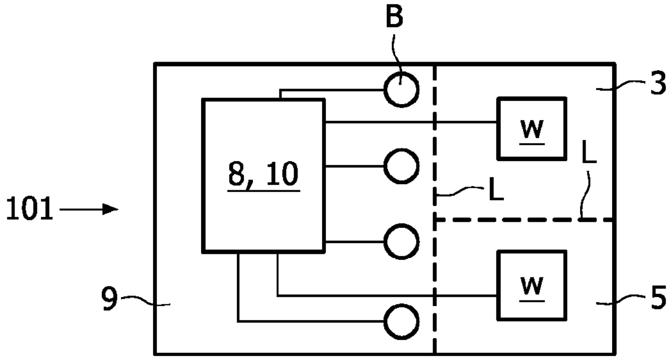
FIG. 2 shows an assay device according to a second embodiment of the invention.

FIG. 2 shows an embodiment of an assay device 101, which differs from the embodiment shown in FIG. 1 in that the device comprises a stack of first carrier parts 3, 5, on one side of the second carrier part, the first carrier parts 3, 5 being detachably coupled to each other. The functioning and operation of the embodiment of FIG. 2 can be substantially the same as that of the FIG. 1 embodiment. This embodiment has the advantage that the device 101 has a more easily understandable layout, and optional interaction options on the recording part (for example the second carrier part 9), for example buttons B, can be placed better relative to the assay parts 3, 5.

Figure 3:
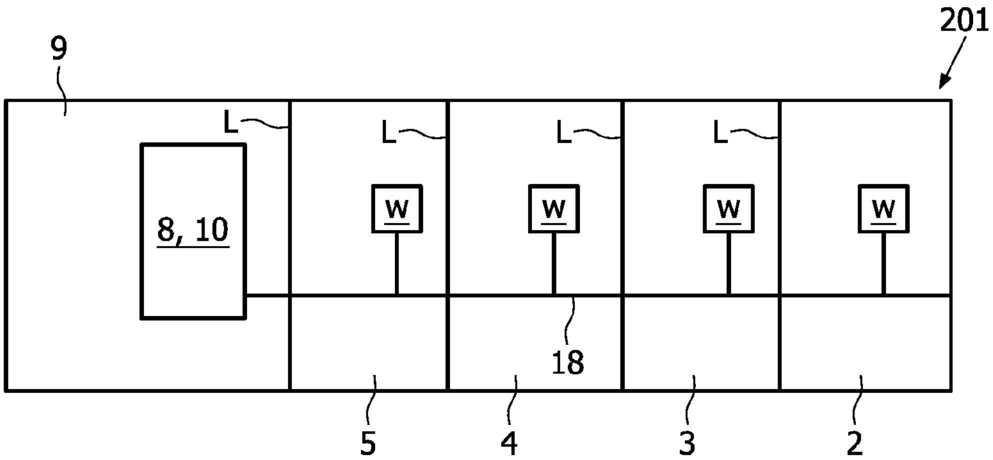
FIG. 3 shows an assay device according to a third embodiment of the invention.

FIG. 3 shows an embodiment of an assay device 201, which differs from the embodiment shown in FIG. 1 in that the device comprises an array of first carrier parts 2, 3, 4, 5, the first carrier parts 2-5 being detachably coupled to each other. Again, the functioning and operation of the embodiment of FIG. 3 can be substantially the same as that of the FIG. 1 embodiment. In the embodiment of FIG. 3, the user can simply start using the outermost assay part 2 and work his way inwards towards the second carrier part 9, while each time detaching one first carrier part 2, 3, 4, 5. In this case, most interaction mechanisms can be stored on the recording part (or second carrier part) 9 of the device 201 to minimize material use.

Figure 4:
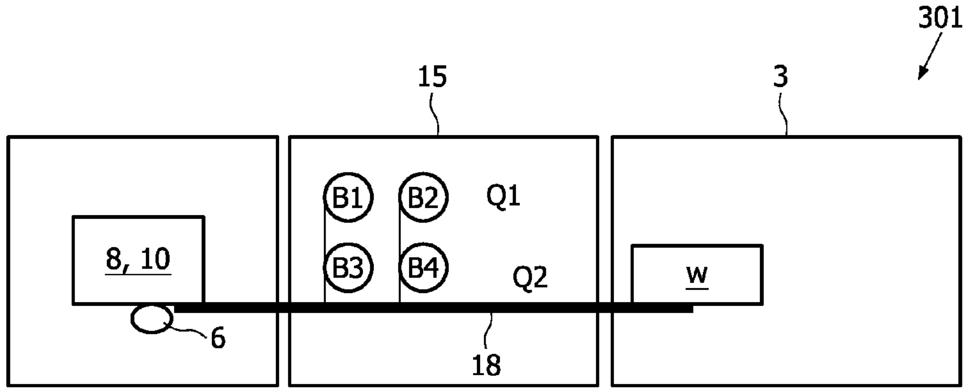
FIG. 4 shows an assay device according to a fourth embodiment of the invention.
Figure 5:
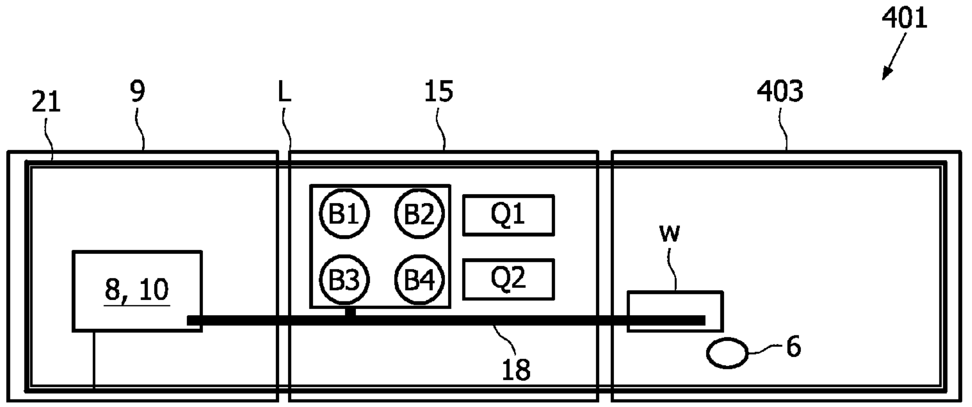
FIG. 5 shows an assay device according to a fifth embodiment of the invention.

FIGS. 4 and 5 show further embodiments of assay devices 301, 401, respectively, each being provided with a user interface, for example multiple-choice buttons B1-B4. The multiple-choice buttons B1-B4 can be associated with respective questions Q1-Q2, for example printed next to the buttons and/or on the buttons. The device can be provided with a specific dedicated carrier part 15 comprising the questions Q and/or buttons B, which dedicated carrier part 15 can be removably connected to the second carrier part 9, which has been provided with a controller 8 and memory 10. Alternatively, the dedicated carrier part 15 and second part 9 may be integrated with each other. Contrary to the above embodiments, the FIGS. 4-5 embodiments are provided with only one first carrier part 3 having a single sample application well w. In the present embodiments, the first carrier part 3 is removably connected to the dedicated user interface carrier part 15.

For example, in the embodiment 301 of FIG. 4, the second carrier part 9 can be provided with a user interaction means 6, for example a test ready indicator. Thus, detaching the first carrier part 3 results in a minimal loss of functionality for the device 301. As the first carrier part 3 is disposed of (it is potentially contaminated), the embodiment of FIG. 4 provides a design where functionality is placed on the recording part when possible. Specifically, any user interaction means, like the test-ready indicator 6 (or the multiple-choice buttons), are placed on the second carrier part 9. In this way, these user interaction means can be used to continue an interaction with the user, even after the carrier part 3 has been detached. For example, the second carrier part 9 needs to be returned to a central processing facility, and the user can be reminded of this aspect by causing the test-ready indicator 6 to blink at intervals, thus focusing attention of the user on the device 301 to be sent in.

The embodiment 401 of FIG. 5 differs from the FIG. 4 embodiment in that the test ready indicator 6 is provided on the first carrier part 403. In FIG. 5, an embodiment of a tear off detection mechanism is shown, the mechanism comprising a loop 21 extending along the outer rim of the assessment device 401, for example an electric wire, which is coupled to the controller 8. As an example, the loop 21 can provide a self-test mechanism, which is to be used by the controller 8 in order to be able to determine whether the device 401 is still intact for assaying a sample. For example, if the carrier of the device 401 is constructed from a paper-like material, rips in the outer rim can be common, and can be detected via the loop 21.

Also, in an embodiment, the assay device 1, for example any of the above-described devices, can be configured to automatically switch from a low power consumption state to a high power consumption state at the start of an assay of a sample, and is preferably configured to switch from a high power consumption state to a low power consumption state after having tested the sample and/or after having stored a test result in the memory device. For example, the device 1 can use a special power conservation strategy. It only powers up the sensor(s) on the assay part during measurement. To realize this strategy, the device determines when the actual assessment starts, and the device is extended with an assessment control unit that is capable of sending, or not sending, power to one or more of the sensor(s). Determining when the assessment unit starts can, for example, be performed using a processor 8 that receives input from a "start assessment" button S (see FIG. 1). Alternatively, the start of the assessment can depend on more characteristics, like sensed environmental circumstances.

Besides, in an embodiment, the assay device 1, for example any of the above-described devices, can contain a self-checking function and can signal to the user that it is operating correctly (or not). An embodiment can be a small LED 26 (see FIG. 1) on the assessment device 1 that should always light up if the card is in operation. The user then knows the card is not operational if the light is off or blinking. The self-test can re-use the self-test mechanisms of the internal components (memory, application well), and for the electronic circuitry on the card use can be made of a tear-detection mechanism to detect if essential circuits are damaged.

Moreover, in an embodiment, the assay device 1 can be configured to provide an operating signal (for example a LED signal via a mentioned LED 26) prior to and/or during proper operation of the device 1. Thus, a user of the device can perceive in a simple manner that the device 1 will start operating and/or is operating, which can provide reassurance and can encourage the user to start, and continue, using the device 1.

Advantageously, the assay system is, or is also, configured to carry out a relatively precise oral glucose tolerance test (OGTT), utilizing the assay device 1. This will be described in the following, referring to FIG. 6.

For example, at least one eatable and/or drinkable product can be provided. In that case, the user can be guided to consume the eatable and/or drinkable product before and/or during using the device to assay a sample of the user. In a further embodiment, the eatable and/or drinkable product can contain glucose, and the assay device 1 is configured to test at least one blood sample for glucose. As an example, the product can be a sweet, wine gum, a glucose-containing beverage, or a different product. Besides, in this case, the disposable assay device 1 can be configured to assay at least two blood samples, for example by being provided with at least two application sample wells w (as in the embodiments of FIGS. 1-5). For example, a user guidance system can be available to provide user guidance to guide the user of the device to test at least a second blood sample after elapse of a predetermined amount of time after testing a first sample. Here, a clock or timer can be provided to measure the elapse of time after the user has applied a first blood sample to a respective application well.

Figure 6:
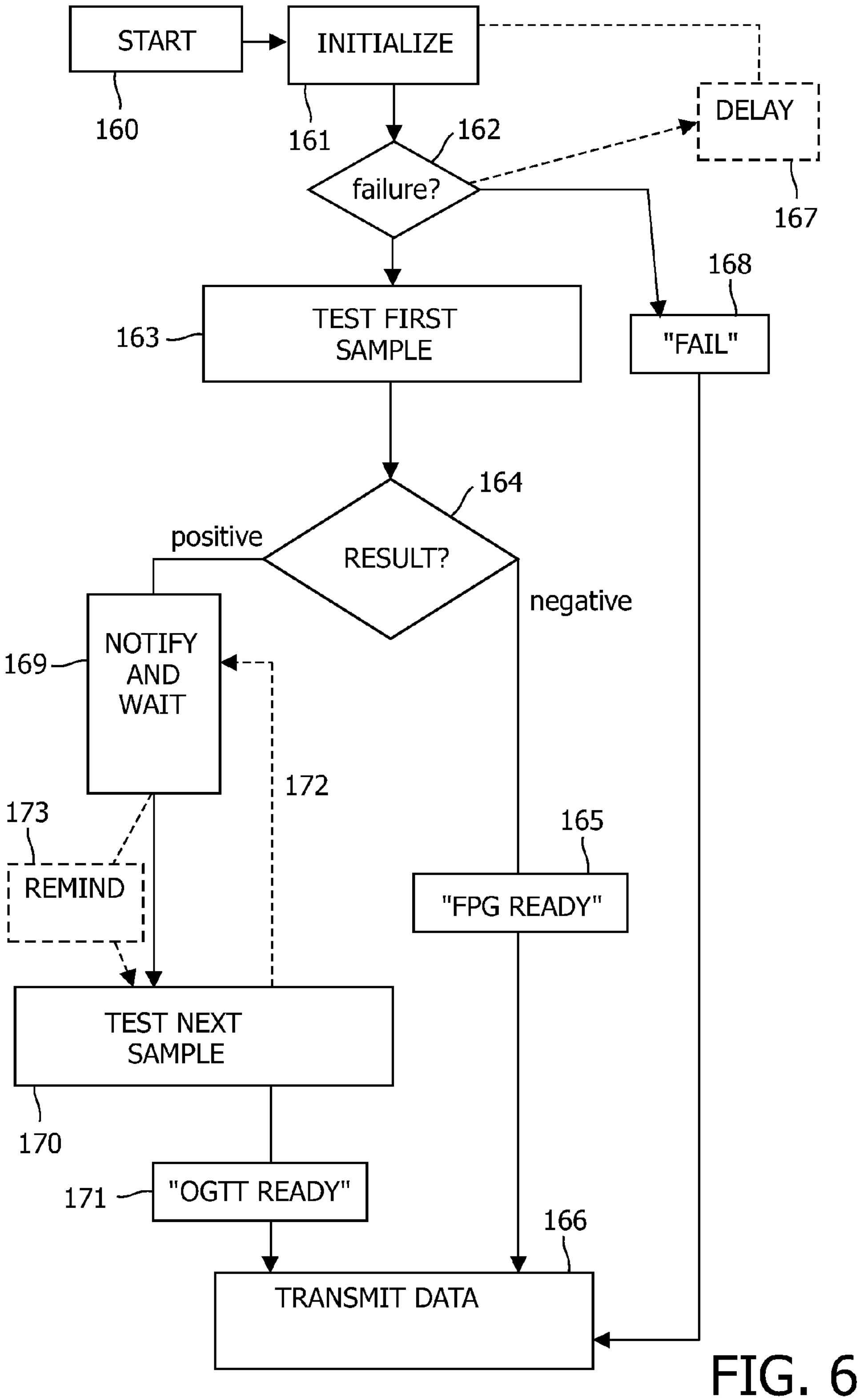
FIG. 6 shows a flow chart of an assay method.

The assay device 1 can be configured to generate a first test result relating to the assaying of the first sample. Also, the user can be guided to assay at least the second sample, depending on the first test result. For example, a second test can be carried out in case a first test result is "assay inconclusive", "assay failed", "device failure" or a similar result. However, preferably, a second test is carried out to turn a FPG test into an OGTT test. As an example, in case the first test result indicates that it is likely that the respective user has (pre-) diabetes, a second glucose test can be performed, a predetermined time period after the first test, to provide an OGTT test to verify the first test result and to provide a much more conclusive OGTT test result. For example, the assay device can be configured to carry out an oral glucose tolerance test, if desired. FIG. 6 depicts a flow chart of a use of such a device.

In FIG. 6, the assaying of user blood can be started by the user (step 160), for example by pressing a specific "start test button" S, or giving a command in any other way to the assay device 1.

A subsequent initialization step 162 can involve asking the user questions Q (as in the FIGS. 4-5 embodiments). The outcome of this step 162 can be that the test is not suitable to the user. In that case, the device 1 can indicate "test is not suitable" in a fail-step 168, which test result can be transmitted to a data processing/remote receiving system 20 (step 166).

Alternatively (as has been indicated by broken lines), a result of the initialization step 162 can be that the user has to wait a certain amount of time before he may use the device. Such a delay is indicated by a delay-step 167. Also, during this step 162 it may be determined whether the user is in a fasting state (see above).

On the other hand, in case the initialization phase succeeds, a first user blood sample can be tested by the device 1 in a first blood test (step 163). For example, a well w of a removable assay part 3 can be available to receive a first blood sample. Optionally, the user can be guided or instructed (for example by a mentioned user guidance system) to consume a mentioned eatable and/or drinkable product, just before, during or after the application of a user blood sample to an application well w of the assay device 1. Preferably, the consumption of the product is at such a time that it does not substantially change the outcome of the first blood test.

In case the first test is "negative" (i.e., chance of pre-diabetes or diabetes is unlikely), a "test ready" indication can be provided (for example "FPG ready", see step 165). Also, information or data relating to the test result can be transmitted to a processing facility 20 (step 166). For example, in the case that the user was in a fasting state just before taking his first blood sample, the first test result can be a FPG test result.

On the other hand, the device 1, or a user guidance system, may require that a more accurate OGTT is performed. This can be the case, for example, when it was found in the initialization step 162 that the user was not in a fasting state. Also, the OGTT test may be required in case the first test result was positive (i.e., there is a likelihood of pre-diabetes or diabetes).

To perform the OGTT test, the device 1 (or user guidance system) can notify the user to wait a predetermined amount of time (step 169; for example 1 hour, 2 hours or a different period). The user can be instructed to take a second blood sample and test the sample, using a second application well w of the device 1 (for example a well w of another removable assay part 5), immediately after lapse of the waiting period. Preferably, a reminder is provided by a user guidance system (step 173), for example via an alarm of the device 1 or via a call from a remote call center, that the waiting period is about to lapse and/or has just lapsed. Then, a second blood sample can be applied and tested (step 170), using the device 1. Thus, an oral glucose tolerance test can be carried out. Optionally, after the testing of a second blood sample, one or more blood samples can be tested after predetermined waiting periods (step 172). Preferably, the device 1 measures the amount of time that has lapsed between the application of the various blood samples to respective application wells, and stores the lapsed time period(s), or stores the times that the samples were applied to the device 1.

After completion of the testing of the at least first and second blood samples, a test ready signal can be provided (for example "OGTT ready", see step 171), and resulting test information can be transmitted in a suitable manner (step 166).

An advantage of the OGTT test is that it is much more reliable than the FPG test. In this way, for example, the assay device 1 can at least perform, or try to perform, a relatively fast FPG test on a user blood sample. Depending on the outcome of this test, or depending on the user's condition, the test can be changed into the OGTT test. In the latter case, the FPG test can simply be used as part of the OGTT test.

Although the illustrative embodiments of the present invention have been described in greater detail with reference to the accompanying drawings, it will be understood that the invention is not limited to those embodiments. Various changes or modifications may be effected by one skilled in the art without departing from the scope or the spirit of the invention as defined in the claims.

It is to be understood that in the present application, the term "comprising" does not exclude other elements or steps. Also, each of the terms "a" and "an" does not exclude a plurality. Also, a single processor or other unit may fulfill functions of several means recited in the claims. Any reference sign(s) in the claims shall not be construed as limiting the scope of the claims.

For example, instead of an entire first device part having to be removed, only the respective application well w can be removable from the device 1. As an example, instead of tearing off an entire carrier part 3, 5, the user can punch out the used application wells w on the assay device. Thus, the main objective of tearing off an assay part is preserved: the biohazardous blood samples are removed. However, it allows closer stacking of multiple application wells, better re-use of other device aspects on the card (which hence are not thrown away now), and enables easier handling for transportation, as the full device is better shaped for transportation than the partial device.

Also, in an embodiment, paper electronics can be combined with smart card technology to improve recycling of materials. It is observed that a major proportion of the materials cost of the device is accounted for by the electronics contained in the recording part. Since the device is primarily single use, it would be advantageous to effectively recycle the materials used. While the assay part contains bio-hazardous materials after use, the recording part does not. By attaching a smart card containing the processor, storage and communication means to the paper electronics containing the other parts of the device, the smart card can be recycled and refurbished. To this aim, as an example, the following steps can be carried out:

1. User sends smart card (attached to rest of recording part) to processing facility.
2. Information is processed.
3. If still present and not re-usable, rest of assay part is removed from smart card.
4. Smart card memory is erased, smart card functioning is checked: is it still ok?
5. If smart card is ok, it is rewritten with new starting information for a new assessment, and attached to a new recording part with attached assay part.

After step 5, there is a new screening device that can be transported to a (different) user.

Besides, the assay device 1 can be provided with a (write-once) display; however, this is not for indicating an assay test result to the user. User interaction on the device 1 is typically a combination of printed text that informs the user about the steps to be taken and possible outcomes of the test, and LED signals to alert the user to the current text to be read. It would be advantageous to show text no sooner than when it is relevant to the user. A display can be added to the device, but this would significantly increase the cost. A low-cost write-once (or write a few times) text display can be created by preparing paper with a chemical like pedot—(poly ethylene dioxide thiophene), which only colorizes when an electrical current is applied to it. In this way, structures (e.g. arrows to guide a user to a next step or texts) can be prepared in advance and made visible when necessary.

Also, preferably, a second carrier part of the assay device can be provided with a memory 10, however, this is not essential.

An application of the invention is in determining whether or not a patient has pre-diabetes or diabetes. However, testing for other diseases using body fluid samples or other sensor mechanisms like galvanic skin response or ECG may also benefit from this invention.

The invention claimed is:

1. A disposable assay device, comprising:
- a plurality of first carrier parts coupled to each other, each first carrier part having a respective sample-receiving area for receiving a sample to be tested;
- at least one second carrier part coupled to the at least one of the plurality of first carrier parts for performing the assay of the samples and forming assay data; and
- a transmitter for transmitting assay data to a remote receiving system,
- wherein at least one of the plurality of the first carrier parts is independently removable from the second carrier part and the remaining plurality of the first carrier parts.

2. The assay device according to claim 1, wherein the plurality of first carrier parts is an array of first carrier parts detachably coupled to each other.

3. The assay device according to claim 1, wherein the plurality of the first carrier parts are each detachably coupled to the second carrier part.

4. The assay device according to claim 1, further comprising weakening lines or perforation lines extending between the first and second carrier parts for independently removing the first carrier parts from the second carrier part.

5. The assay device according to claim 1, wherein the at least one second carrier part includes a memory device and is configured to record each assay result in combination with identification information of a respective first carrier part, leading to that assay result, in the memory device.

6. The assay device according to claim 1, wherein the at least one second carrier part includes a memory device and is configured to record each assay result in combination with time information concerning a respective assay, leading to that assay result, in the memory device.

7. The assay device according to claim 1, wherein the at least one second carrier part includes a memory device and is configured to detect the removal of a first carrier part, and to record a time of the removal of the first assay part, in the memory device.

8. The assay device according to claim 1, wherein the first and second carrier parts are configured to assay at least two blood samples, provide at least one assay result, and carry out an oral glucose tolerance test.

9. The assay device according to claim 1, further comprising a test-ready indicator on at least one of the plurality of first carrier parts.

10. The assay device according to claim 1, wherein the second carrier part includes a user interface having multiple-choice buttons.

11. The assay device according to claim 1, wherein the second carrier part comprises a memory device configured to store assay results relating to tested samples, and a controller.

12. A method of assaying, the method comprising acts of:

providing a disposable assay device including a plurality of first carrier parts coupled to each other and a second carrier part coupled to at least one of the first carrier parts;

applying one or more samples to a selection of the first carrier parts to test the samples for the presence of one or more analytes;

storing resulting test results in a memory; and removing each first carrier part of the selection from the plurality of first carrier parts and second carrier part after having used that selection of the first carrier parts.

13. The method according to claim 12, wherein first carrier parts are used in sequence, with a predetermined intermediate time period of approximately 24 hours.

14. The method according to claim 12, further comprising an act of: transmitting assay data to a remote receiving system, the assay data comprising one or more assay results information concerning failure of the assaying.

15. The method according to claim 14, wherein the receiving system receives the assay data and determines, using the received assay data whether a respective assay data is a negative or positive assay result, whether the assay result is inconclusive, whether the assaying has failed, and why the assaying has failed.

16. A disposable assay device to assay one or more samples, the disposable assay device comprising:

a plurality of sample application areas removably coupled to each other for receiving the one or more samples to be assayed;

a controller detachably coupled to at least one of the plurality of sample application areas for performing the assay of the one or more samples and forming assay data;

a transmitter for transmitting the assay data to a remote receiving system; and one or more assay context sensors to monitor one or more assay context factors wherein at least one of the plurality of sample application areas is independently detachable from the controller and the remaining plurality of sample application areas.

* * * * *